(12) United States Patent
Scharlack et al.

(10) Patent No.: US 6,172,744 B1
(45) Date of Patent: Jan. 9, 2001

(54) METHOD AND APPARATUS FOR PERFORMING SPECTROSCOPIC ANALYSIS WITH APPLICABILITY TO SAMPLES WITH TURBIDITY AND ABSORPTION

(75) Inventors: Ronald S. Scharlack, Brookline; James J. Childs, Franklin, both of MA (US)

(73) Assignee: Bayer Corporation, Tarrytown, NY (US)

(*) Notice: Under 35 U.S.C. 154(b), the term of this patent shall be extended for 0 days.

(21) Appl. No.: 09/459,129

(22) Filed: Dec. 10, 1999

Related U.S. Application Data

(63) Continuation of application No. 09/159,944, filed on Sep. 24, 1998.
(60) Provisional application No. 60/060,018, filed on Sep. 25, 1997.

(51) Int. Cl.$^7$ ............................ G01N 33/48; G01N 31/00
(52) U.S. Cl. .................................. 356/39; 702/23; 702/28
(58) Field of Search ............................ 356/39, 432, 300, 356/319; 702/19, 21, 23, 27, 76, 28

(56) References Cited

U.S. PATENT DOCUMENTS

| 4,174,202 | 11/1979 | Simpson | 23/230 |
|---|---|---|---|
| 4,800,282 | 1/1989 | Nishimura | 250/461.1 |
| 5,046,846 | 9/1991 | Ray et al. | 356/326 |
| 5,125,747 | 6/1992 | Sayegh et al. | 356/407 |
| 5,724,268 * | 3/1998 | Sodickson et al. | 702/23 |

FOREIGN PATENT DOCUMENTS

| 0210417 | 2/1987 | (EP) . |
|---|---|---|
| 0693682 | 1/1996 | (EP) . |
| 54-084781 | 7/1979 | (JP) . |
| 94/08237 | 4/1994 | (WO) . |

OTHER PUBLICATIONS

Berger, A. et al., "An Enhanced Algorithm for Linear Multivariate Calibration", *Anal. Chem.*, 70, pp. 623–627 (1998).

Latimer, P. et al., "Absorption Spectrophotometry of Turbid Suspensions: A Method of Correcting for Large Systematic Distortions", *Archives of Biochemistry and Biophysics*, 98, pp. 274–285 (1962).

MacRae, R. et al., "Spectral Transmission and Scattering Properties of Red Blood Cells", *Journal of the Optical Society of America*, 51/12, pp. 1366–1372 (1961).

Orttung, W.H. et al., "Refractive Index Dispersion in Equine Hemoglobin Solutions", *Journal of Physical Chemistry*, 69/9, pp. 3188–3190 (1965).

* cited by examiner

*Primary Examiner*—Frank G. Font
*Assistant Examiner*—Zandra V. Smith
(74) *Attorney, Agent, or Firm*—Weingarten, Schurgin, Gagnebin & Hayes LLP

(57) ABSTRACT

A method for analysis of samples having turbidity and/or high absorption is disclosed. The analysis incorporates several factors that affect transmittance or absorption. These factors may include: absorption as measured in a non-turbid sample, scattering losses due to particles and limitations of the measurement device as measured in a non-absorbing sample, additional scattering losses due to sample absorption, variable path length effects due to the sample, and variable path length effects due to the measurement device. By taking into account additional factors that affect transmittance or absorption, a more accurate analysis is achieved.

11 Claims, 14 Drawing Sheets

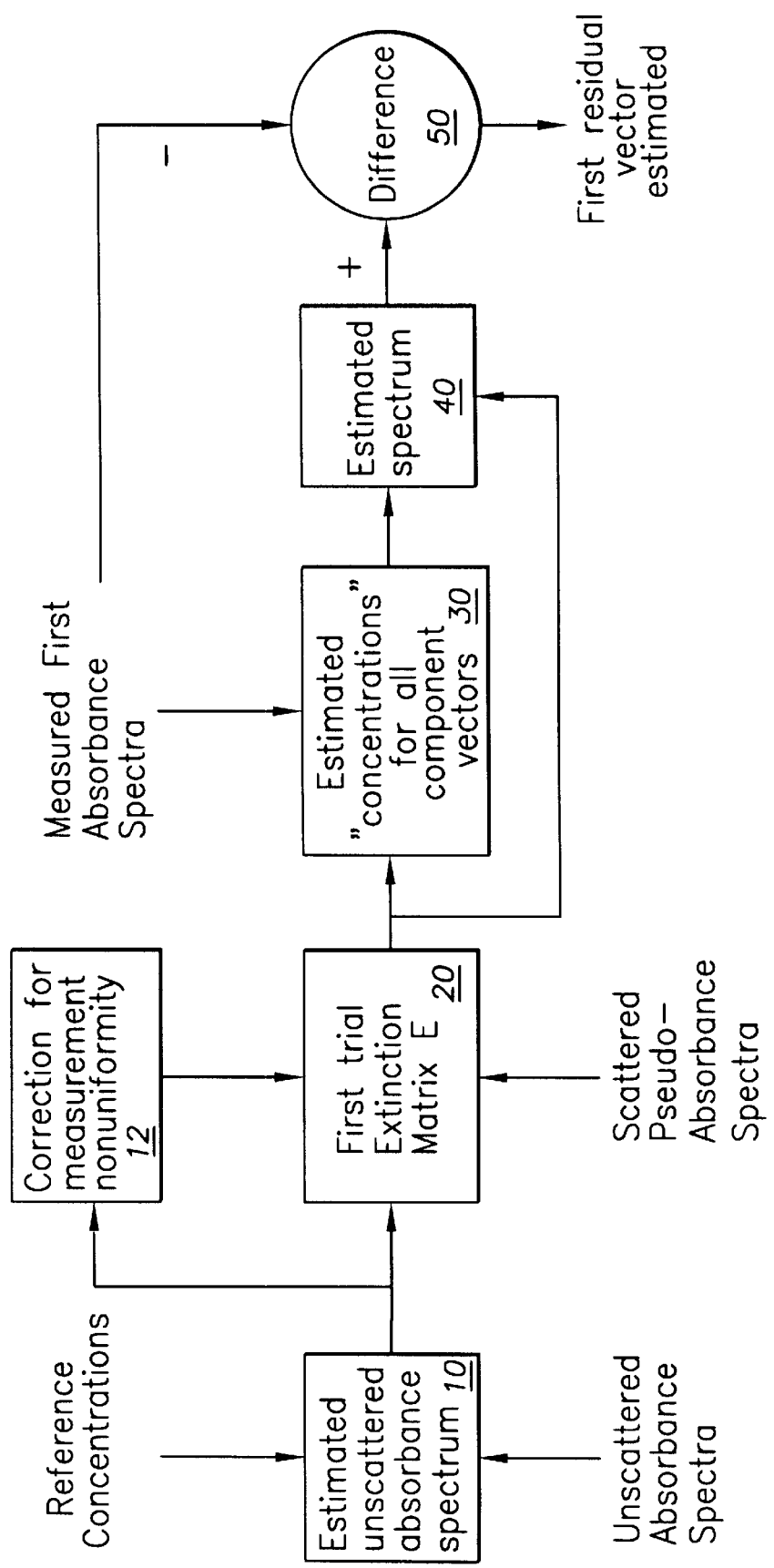
FIG. 4A  Calculation of Residual Spectra

FIG.5A  Residual Vector for an Oxygenated Blood Sample
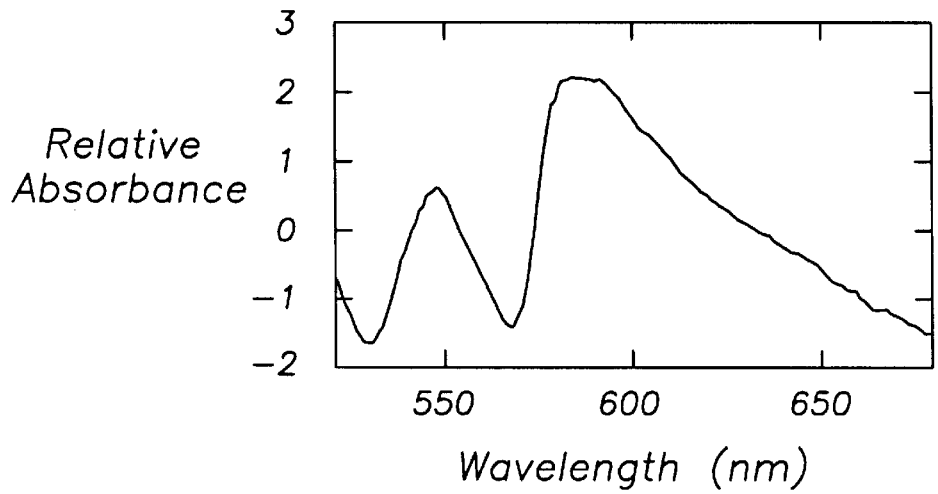
FIG.5B  Residual Vector Associated with The Major Hemoglobin Species
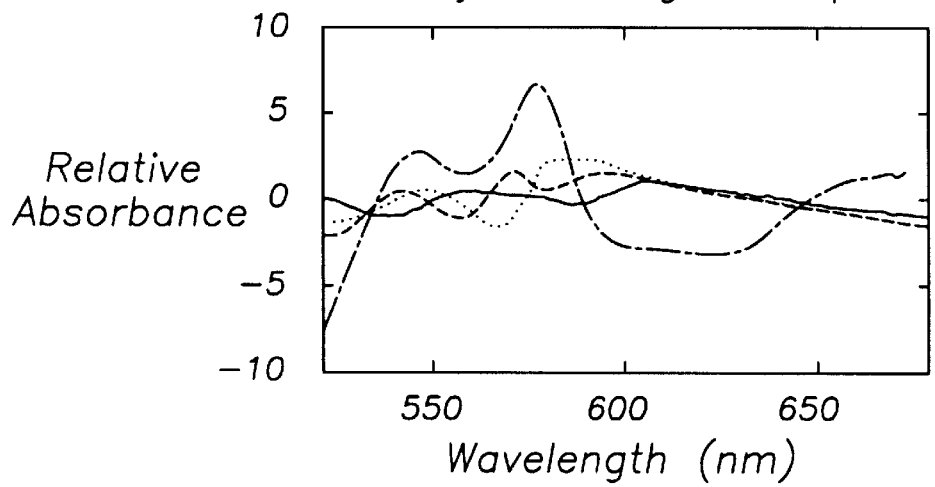
—·— MetHb Residual
········ O2Hb Residual
------ COHb Residual
——— HHb Residual

METHOD AND APPARATUS FOR PERFORMING SPECTROSCOPIC ANALYSIS WITH APPLICABILITY TO SAMPLES WITH TURBIDITY AND ABSORPTION

CROSS REFERENCE TO RELATED APPLICATIONS

This application continuation of patent application Ser. No. 09/159,944, filed Sep. 24, 1998, which claims priority under 35 U.S.C. § 119(e) to provisional patent application Ser. No. 60/060,018, filed Sep. 25, 1997, both of which are incorporated herein by reference.

STATEMENT REGARDING FEDERALLY SPONSORED RESEARCH OR DEVELOPMENT

Not Applicable

BACKGROUND OF THE INVENTION

Multivariate techniques such as classical least squares (CLS), partial least squares (PLS) and principal component regression (PCR), have often been applied in the spectroscopic analysis of samples that contain multiple components of interest. These techniques provide accurate estimates of the components' concentrations when certain assumptions are satisfied: (1) the signal strength of each component's spectrum is proportional to that component's concentration and (2) the component spectra add linearly. Note that in some cases the signal does not satisfy these conditions but a function of the signal does. For example, in transmission-absorption measurements where the Lambert-Beer law applies the transmitted signal does not satisfy (1) or (2) but the logarithm of the transmitted signal (i.e., the absorption spectrum) does.

Important examples of samples that do not satisfy the linearity assumptions above are turbid or heterogeneous samples. In optical spectroscopy, radiation that propagates through a turbid sample is scattered and its path is altered. The alteration of the light path has two possible consequences; the light may miss the detector and not be detected at all or the detected, scattered light may have traversed the sample in a randomly circuitous way. Both consequences affect the absorption spectra, and therefore affect concentration estimates (particularly in applications that require fixed, known sample path lengths in order to unambiguously determine component concentrations). The latter consequence means that the detected signal is an average of measurements of the sample at multiple path lengths. Further, if the turbid sample is heterogeneous and has localized, rather than uniformly, distributed absorbing components some light rays may pass through undiminished (zero path length) and be neither scattered nor absorbed. This will also contribute to erroneous interpretation of the sample's absorption spectrum. A particular example of this arises in the analysis of hemoglobin content in blood and we will use this illustrative example throughout since it contains all the salient features that this technique addresses. However, it should be clear that the work described in this patent is not limited to this application.

Whole blood is the natural state of blood consisting of virtually transparent plasma within which floats red blood cells (that contain the absorbing pigment, hemoglobin, of interest), lipids, white blood cells, platelets, and a host of other objects. Several considerations must therefore be addressed in order to design an instrument that will provide an accurate measure of the hemoglobin content. One consideration is light scatter that traditionally has been minimized by breaking the red blood cells to form a homogenous mixture called lysed blood. While scatter is not completely eliminated with this approach (lipids, cell stroma, and other large particles are still present) the nonlinearities induced by the residual scatter are small enough to be neglected or treated with simple corrections to account for their affects. Other considerations are the sample cell dimensions and optical design to insure that the measurement takes place within an optimal absorption range (adequate signal-to-noise) and at fixed, known path length of the apparatus, respectively. Absorption can be adjusted by known dilution of the blood or by appropriate choice of sample cell dimensions (i.e. path length). The optical designer must insure that the incident source light is adequately collimated to create a unique path length and that enough transmitted light is collected to satisfy signal strength requirements.

With the desire to measure unaltered, whole blood, prior attempts to perform analysis on turbid, absorbing samples have required specialized apparatus that allow for the collection of the directly transmitted light and as much of the scattered light as possible. It would be desirable to perform accurate analysis of turbid, absorbing samples without having to precondition the sample or without having to utilize specialized light collection devices. Further, it would also be desirable to relax the stringent requirements on optical design (i.e., collimated probe light beam) in the analysis of non-turbid samples. The invention described in this patent provides for accurate analysis of samples without the above-mentioned constraints.

BRIEF SUMMARY OF THE INVENTION

A method and apparatus for performing analysis of turbid and/or highly absorbing samples is disclosed. The method described here applies a Linear Least Squares algorithm to the nonlinear problem described above although other multivariate techniques could be used as well. In addition to the usual vectors that describe the extinction of the absorbing components of interest, several other vectors that accurately model the nonlinear effects are included in the analysis. The Least Squares analysis is iteratively applied to a sample spectrum with proper adjustments made to certain vectors at each iteration. The resulting component concentrations converge quickly to estimates that are more accurate than those obtained without consideration of these effects.

The analysis applies Beer-Lambert's law to interpret absorption spectra of transmitted or reflected signals. Several factors affecting the light transmitted through or reflected from the sample are included; absorption of the pigment of interest, scattering losses due to particles and to limitations of the collection device, and multiple path length effects. The absorption term consists of the known extinction coefficients as is commonly known in the field. There are several scatter loss terms corresponding to the various origins of scatter in the sample. Two terms account for Rayleigh-type scatter losses that have simple power law dependence on the wavelength of light. In the case of a whole blood application where the absorbing pigment is localized in red blood cells, a third term is included as a residual vector (see below) that accounts for scatter losses with a more complicated dependence on wavelength. In fact, this scatter loss term arises partly from instrumental design (inability to collect all the scattered light) and partly from anomalous dispersion whereby the real part of the refractive index (of the red blood cells) contains a contribution from the imaginary part (Kronig-Kramers relations). Note that the imaginary part of the refractive index is the extinction (absorption) coefficient of the absorbing hemoglobin pigment. Since the exact form of this scatter term's dependence on wavelength is not easily derived for multiple scatter events and since it is dependent on instrument design, it is determined as an average residual (across several instruments) and used as a compensation vector in the Least-Squares analysis. A fourth term is derived and included as a vector to account for the multiple path length effects mentioned above. Note that this effect may be due not only to scatter but also to sample obstructions such as bubbles and clots, to the measurement device (e.g., non-collimated light), and to other nonlinear effects such as the distribution of the number of cells sampled by a light ray. By taking into account these factors that affect transmittance or reflectance, this invention provides a more accurate analysis of component concentrations.

BRIEF DESCRIPTION OF THE SEVERAL VIEWS OF THE DRAWINGS

The invention will be more fully understood from the following detailed description and the accompanying drawings in which:

FIG. 4A is a flow chart for the calculation of the residual spectra;

FIG. 5A is a graph of a residual vector for oxyhemoglobin;

FIG. 5B is a graph of the residual vectors for all principal hemoglobin components;

DETAILED DESCRIPTION OF THE INVENTION

Figure 1:
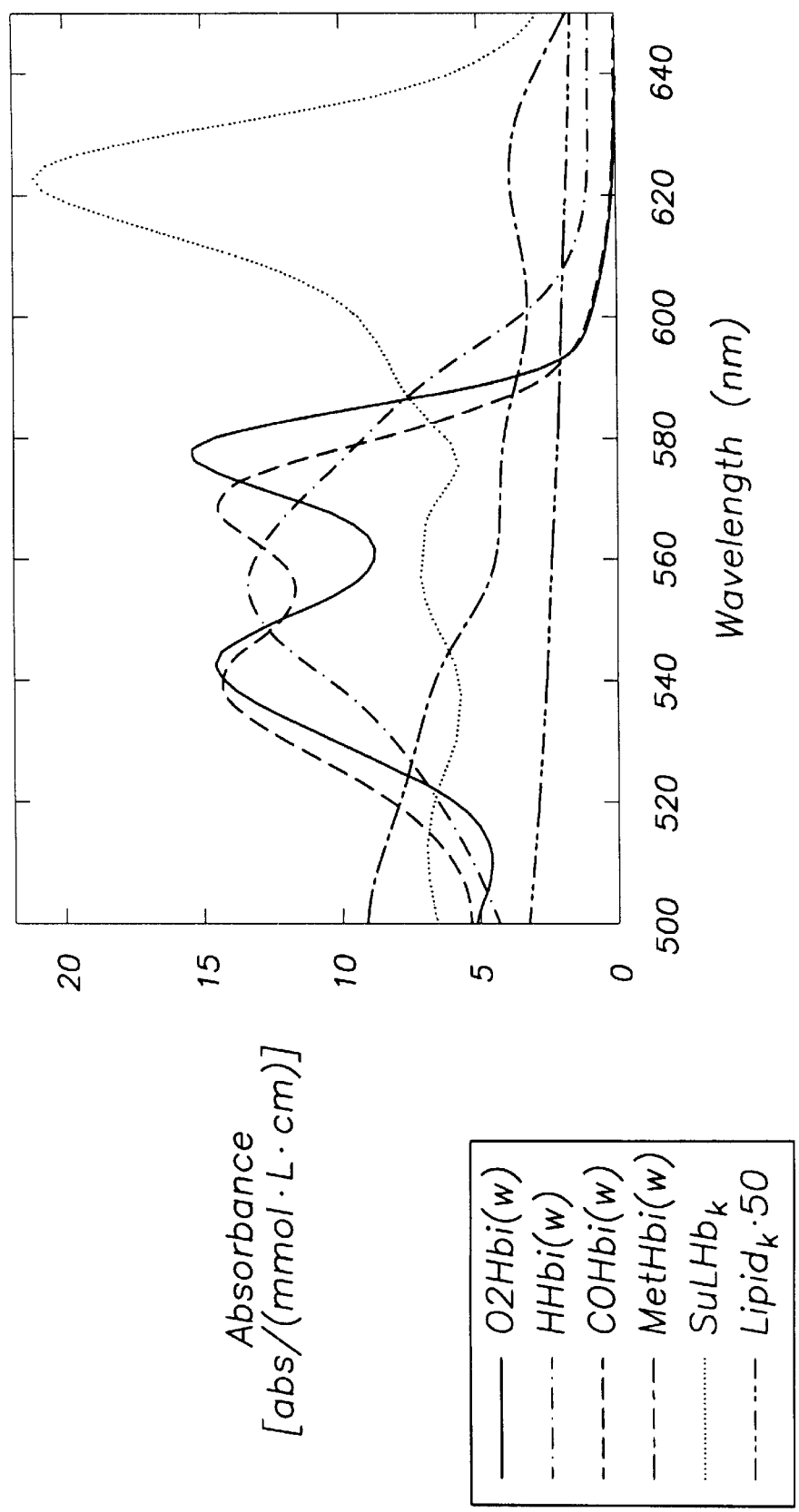
FIG. 1 is a graph of the spectra of the major absorbing blood components.

The present invention provides the accurate determination of component concentrations utilizing an improved analysis of spectra affected by turbidity and/or high sample absorption. The invention accounts for nonlinear effects arising from turbidity and sample absorption with an iterative algorithm that uses conventional linear analysis. Nonlinear effects due to turbidity and high sample absorption have been described in the literature (see for example "The Flattening of Absorption Spectrum of Suspensions, as Compared to that of Solutions", I. N. M. Duysens, *Biochimica Et Biophysica Acta*, Vol. 19 (1956), pp1–12, "Spectral Transmission and Scattering Properties of Red Blood Cells", R. A. MacRae, J. A. McClure, and P. Latimer, *Journal of the Optical Society of America*, Vol. 51, No. 12, (December 1961), pp 1366–1372, and "Refractive Index Dispersion in Equine Hemoglobin Solutions", W. H. Orttung and J. Warner, *The Journal of Physical Chemistry*, Vol. 70 (1966), pp 3188–3190). However, no method prior to this invention has included these nonlinear effects in an analysis that both explains how they arise and provides a more accurate estimate of component concentrations. The understanding gained by this approach leads to the application of this analysis to a host of different and seemingly unrelated phenomena.

The use of the present invention is taught by way of example, but the example is not intended as a limit on the applicability of the invention. Absorption spectroscopy for the analysis of hemoglobin in whole blood is used as an example since whole blood is a heterogeneous solution that exhibits turbidity and high absorption over certain spectral ranges. The invention is useful with other spectroscopic techniques and samples where similar nonlinear effects are present.

Absorption measurements in whole blood or tissue are difficult to analyze because of sample turbidity, high absorption (in certain spectral ranges), and inhomogeneity. Turbidity causes the probing light beam to be scattered, which causes a partial loss of probe signal (some scattered light does not reach the detector) or causes the probe beam to traverse multiple paths through the sample as it travels from the source to the detector. The instrument configuration itself contributes to this effect: The optical design will determine how much light can be lost from the detector. Also, the sample cell dimensions (i.e., path length) and optical design (e.g., degree of probe beam collimation) will determine how much the probe beam's path will deviate from a single, unique path. Further, inhomogeneities in absorption (e.g. hemoglobin isolated in red blood cells that float in plasma) result in probe beam light rays sampling a distribution of absorbers. The consequence of this distribution of absorbing particles sampled by a light ray is analogous to that of a distribution of path lengths in a homogeneous absorbing sample. Both effects are measured with the approximations herein described. Note that since absorption instruments typically measure sample transmittance, and since sample transmittance is nonlinearly related to sample absorption, an averaging of transmittances doe not result in an average absorption. The present invention provides means for treating these measurement effects during the analysis of sample concentrations.

Absorption spectroscopy uses data pretreatment by converting the measured sample transmittance into sample absorption—as is well known in the art. The logarithmic relationship of sample absorption to sample transmittance is given by the following equations:

$$A = -\log(T)$$

and $$T = I/I_o$$

where:
A is the calculated absorption,
T is the calculated transmittance,
I is the measured intensity due to the sample, and
$I_o$ is the measured intensity with a blank sample.

In multivariate analysis multiple measurements are made to permit the estimate of concentrations in samples with several components. In absorption spectroscopy measurements at multiple wavelengths of light are often used to provide the spectral information needed for an accurate analysis. Vectors and matrices are used to simplify the equations. The use of vectors in column or row format depends on the preference of the writer. In the description of this invention vectors are assumed to be in column format and annotated with small, boldface letters. However, this notation and format does not limit the scope of the invention. Matrices will be denoted with capital, boldface letters.

The measured spectrum of an ideal sample can be described as:

$$a = E * c$$

where:
a is the column vector for the sample's absorption spectrum with each row element corresponding to sample absorption at a particular wavelength of light,
E is a matrix of column vectors, each representing the absorption spectrum (extinction) of a component or factor at particular wavelengths, and
c is a column vector describing the concentrations of the components and factors in E (including the scatter terms).

In an analysis of lysed and non-turbid blood for concentrations of the four principal forms of hemoglobin, oxyhemoglobin ($O_2Hb$), deoxyhemoglobin (HHb), carboxyhemoglobin (COHb) and methmoglobin (MetHb), the E matrix is formed by the four vectors representing the four absorption spectra (extinction coefficients) of these components as in the following equation:

$$E_{lysed} = [e_{HHb}\ e_{o2Hb}\ e_{COHb}\ e_{MetHb}],$$

where $e_{Hb}$ denotes the column vector for the corresponding hemoglobin. These spectra are shown in FIG. 1.

Figure 2A:
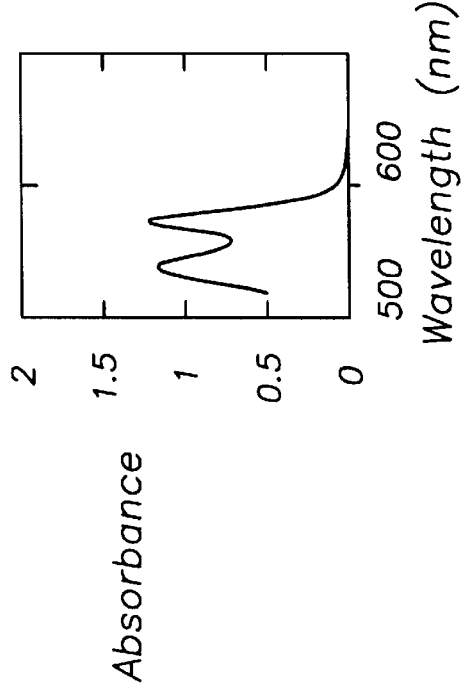
FIG. 2A is a plot of an absorption spectrum of an unlysed blood sample.
Figure 2B:
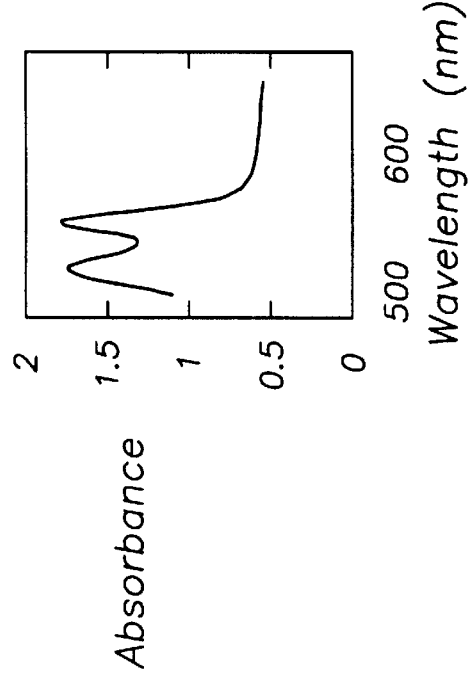
FIG. 2B is a plot of an absorption spectrum of a lysed blood sample.
Figure 2C:
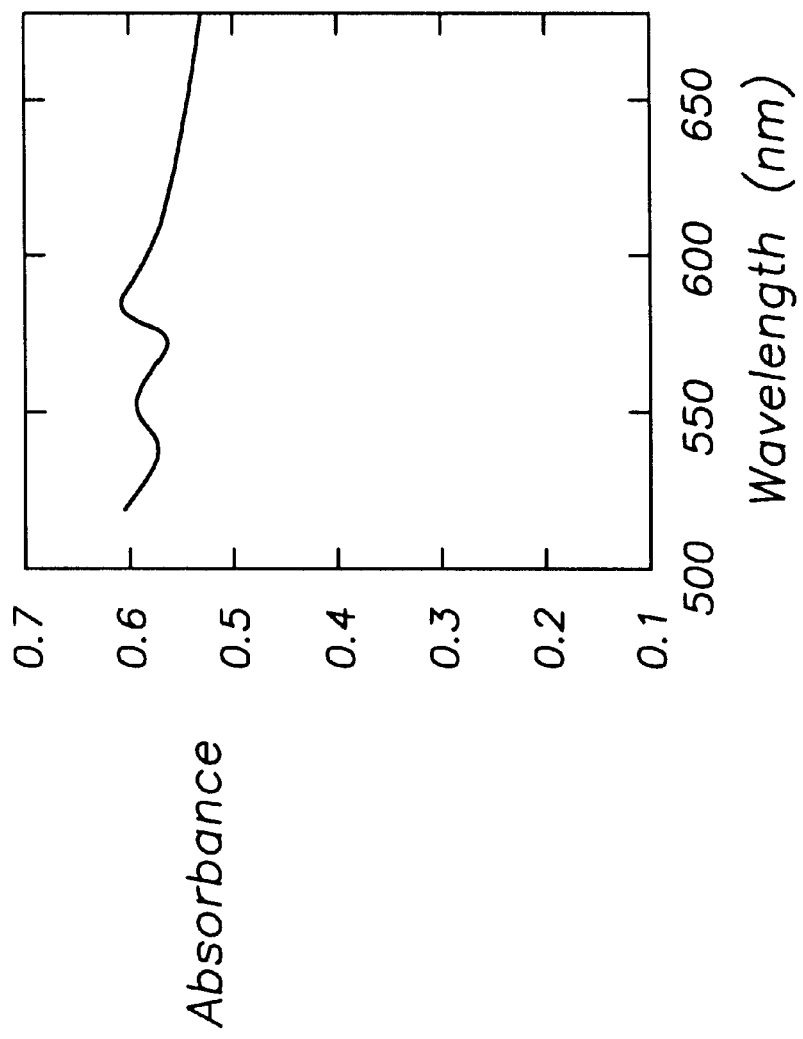
FIG. 2C is a graph of the difference between the spectra of FIG. 2A and FIG. 2B.

This model of absorption is adequate for determining component concentrations in homogenous samples with low turbidity. A spectrum of such a sample is shown in FIG. 2A, the absorption spectrum of a whole or unlysed blood sample containing a high fraction of oxyhemoglobin. For comparison, the absorption spectrum of the same blood but in a lysed state is shown in FIG. 2B. Additional loss of light is immediately apparent in the unlysed sample as it exhibits an overall higher absorption than the lysed. However, the difference between the absorption spectra of whole and lysed blood (see FIG. 2C) is seen to be more than just a uniform (wavelength independent) increase in absorption.

To address the role of scatter, the invention expands the simple model above to include terms as shown in the following equation.

$$a = E_{n1} * c_{n1}$$

where:
$E_{n1} \equiv [E|f(a)]$
where f(a) are additional vectors that describe the scatter terms, and
$c_{n1} \equiv [c/c_{f(a)}]$
where $c_{f(a)}$ is the concentration associated with the scatter terms.

One important consequence of scatter in the measurement of turbid samples is that the incident probe beam can take multiple paths on its way to the detector. This can occur in turbid, lysed blood where the absorbing pigment is homogeneously spread throughout the sample but stroma, lipids, and other scattering particles cause deviations in the path sampled by the light. In this case, light transmitted through the sample can be modeled with a distribution function in absorbing path lengths. The multiple path length effect also occurs in whole blood where the absorbing pigment is localized within the red blood cells that cause the light path to deviate so that a given ray of light will encounter a number of red blood cells. At each encounter with a cell, there is a subsequent reduction in light strength due to absorption. In this case, light through the sample can be modeled with a distribution function for the number of red blood cells encountered but this is essentially equivalent to a distribution function in absorbing path lengths. As described above, this gives rise to a non-linearity in absorption. An excellent correction for this non-linearity is to approximate the effect using the square of the estimated absorption spectrum in a non-turbid or pure sample. The analysis found in Appendix A provides insight into the source of this correction.

The use of the square of the estimated non-turbid spectrum in the present invention is described below. This example makes use of CLS analysis, but can be used with other forms of analysis. The first step in the analysis is to provide an estimate for the relative concentrations of the components in the sample. The portion of the matrix, E, consisting of the absorption vectors as measured in a non-turbid, pure sample (i.e., only the extinction coefficients of hemoglobin) are multiplied by the estimated concentration vector for the hemoglobin components of interest, $C_{hemo\_est}$. (A scale factor can be applied to correct for path length.) The resulting vector in the hemoglobin analysis will be referred to as the pure spectrum (vector). The square of this vector is calculated by squaring the absorption at each of the measurement wavelengths (i.e. squaring each component of the vector). This spectrum is referred to as the lysed$^2$ spectrum (taken from the hemoglobin analysis example) and provides an additional pseudo-absorption column vector in the E matrix that corrects for the various multiple path length effects described above. Since the lysed² vector is determined by the estimated concentrations of components that, in turn, are affected by the lysed² vector, the analysis requires nonlinear techniques for solution described below.

Additional terms are also added to partially compensate for the light loss due to particle scattering. Two separate scaled-wavelength power law terms are used in the hemoglobin analysis. One term provides an approximation based on a small exponent (0.2 has been found to be suitable, $\sim\lambda^{-0.2}$) and the second term provides an approximation based on a larger exponent (2.5 has been found to be suitable, $\sim\lambda^{-2.5}$) The use of two separate terms to approximate an intermediate power law term was found to be satisfactory and simplifies the analysis. An iterative method using a single power law term with a variable exponent has also been successfully applied.

Adding columns to the original E matrix (which was comprised only of the extinction vectors of the components of interest) forms a new matrix, $E_{trial}$. These additional columns are the vectors for the power law scattering and Lysed². This new matrix is a trial matrix because the column representing the Lysed² vector will be modified at each iteration of the calculation.

$$E_{trial} = [E_{ext}\ Scat_1\ Scat_2\ lysed^2]$$

and $$lysed = E_{ext} * c_{hemo\_est}$$

where:
- $E_{ext}$ is the matrix of extinction vectors of the absorbing components of interest (the original E matrix),
- $Scat_1$ and $Scat_2$ are the power law vectors used to represent scatter, and
- $c_{hemo\_est}$ is the vector of estimated concentrations of the components of interest (hemoglobin in the example described here),
- lysed is the lysed vector (spectrum) that does not include any scatter effects. It is also referred in the text as the pure vector (or spectrum) since it contains only the spectrum of the absorbing pigments.

The classical least squares estimate for concentrations of each of the components and pseudo-components is given by:

$$C_{trial} = (E^T_{trial} * E_{trial})^{-1} * E^T_{trial} * a_{measured}$$

where:
- $E_{trial}$ is the combined spectra matrix, $E^T_{trial}$ it's transpose, and $c_{trial}$ is the vector of all estimated concentrations.

The new concentrations of the absorbing components of interest (the components of $c_{trial}$ corresponding to the absorbing components) are now used in the new vector, $c'_{hemo\_est}$, to calculate a new lysed-squared vector and a new $E'_{trial}$ matrix is formed with this vector. This process is repeated for a fixed number of iterations, until an error limit is reached, or until the improvement in error by resulting iterations is below a threshold, as is known to those skilled in the art. One example uses an error measured by the root mean square of the residual spectral error but other similar error metrics can be used.

Referring now to FIG. 4A, a flow chart of the method to determine a residual vector for an unknown sample component or effect(s) is described. At the first step, 10, an estimated pure absorption spectrum is determined from the known absorption spectra (i.e., extinction coefficients) of the absorbing pigments of interest and their estimated reference concentrations. This pure absorption spectrum consists only of the spectra of the absorbing component pigments (i.e., hemoglobin) free from scatter or other multiple path length effects. At the next step 20, a first trial extinction matrix is formed from the estimated pure absorption spectrum of step 10, the pseudo-absorption spectra of the various kinds of scatter, and the estimated spectral correction for path nonuniformity 12, i.e. the multiple path length effect. The estimated spectral correction is the modification of the pure absorption spectrum to provide a component for correcting for path nonuniformity through the use of the lysed² vector. At step 30, concentrations of all component vectors are determined by analysis (e.g. CLS) of the measured absorption spectrum using the first trial extinction matrix of step 20. An estimated spectrum is then obtained at step 40 from the first trial extinction matrix and from the concentrations for all component vectors determined in step 30. As shown in step 50, the difference between the estimated spectrum and the measured absorption spectrum yields a residual vector. This process 10 is then repeated for all measurements until all vectors are estimated for the initial set of conditions or instrument. A second set of residual vectors can be generated using the same process 10 with a second data set. The first residual vectors are added (with appropriate restraints) to the first trial extinction matrix to form a second trial extinction matrix.

Figures 1, 4B:
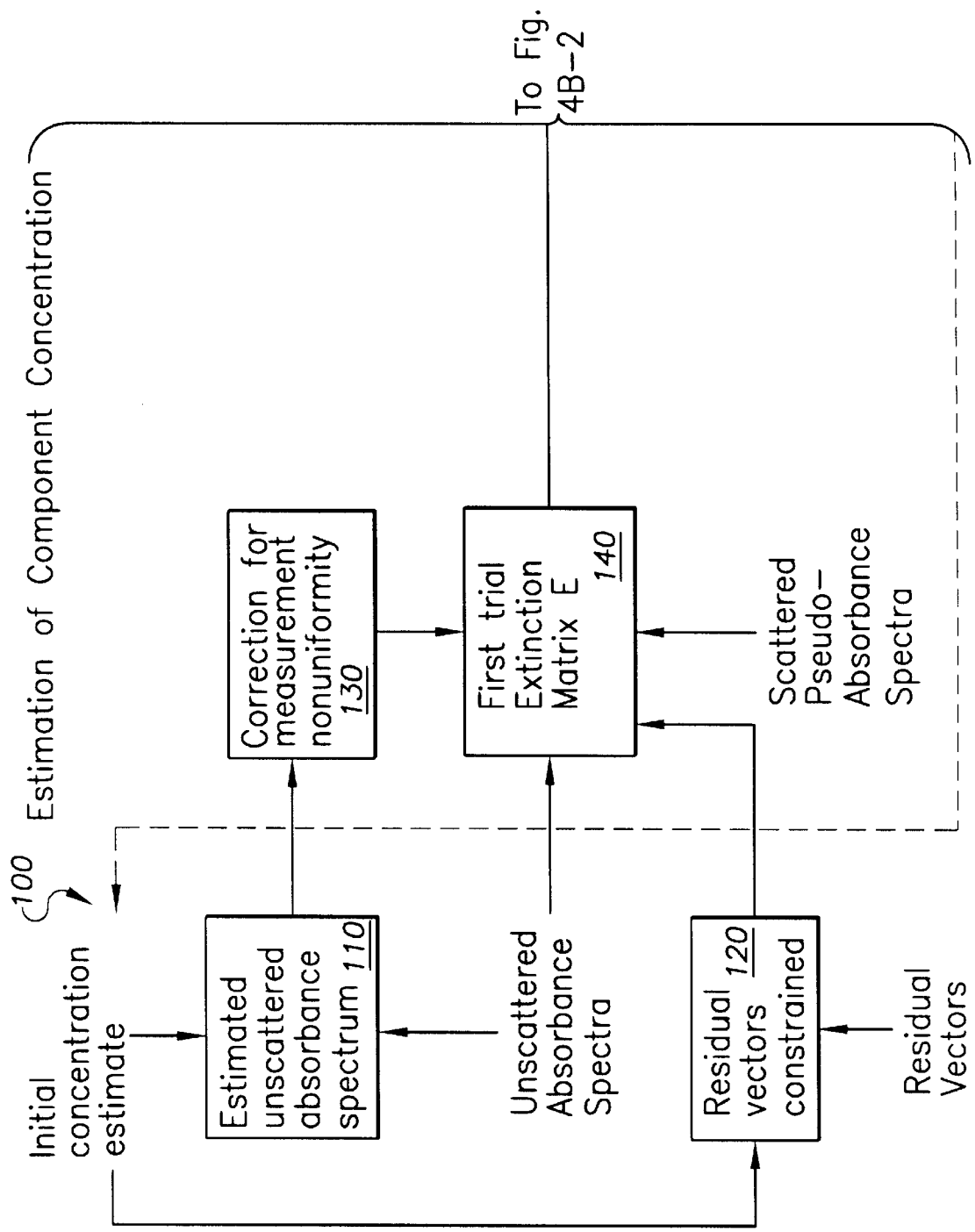
FIG. 4B is a flow chart for the estimation of component concentration.
Figures 2, 4B:
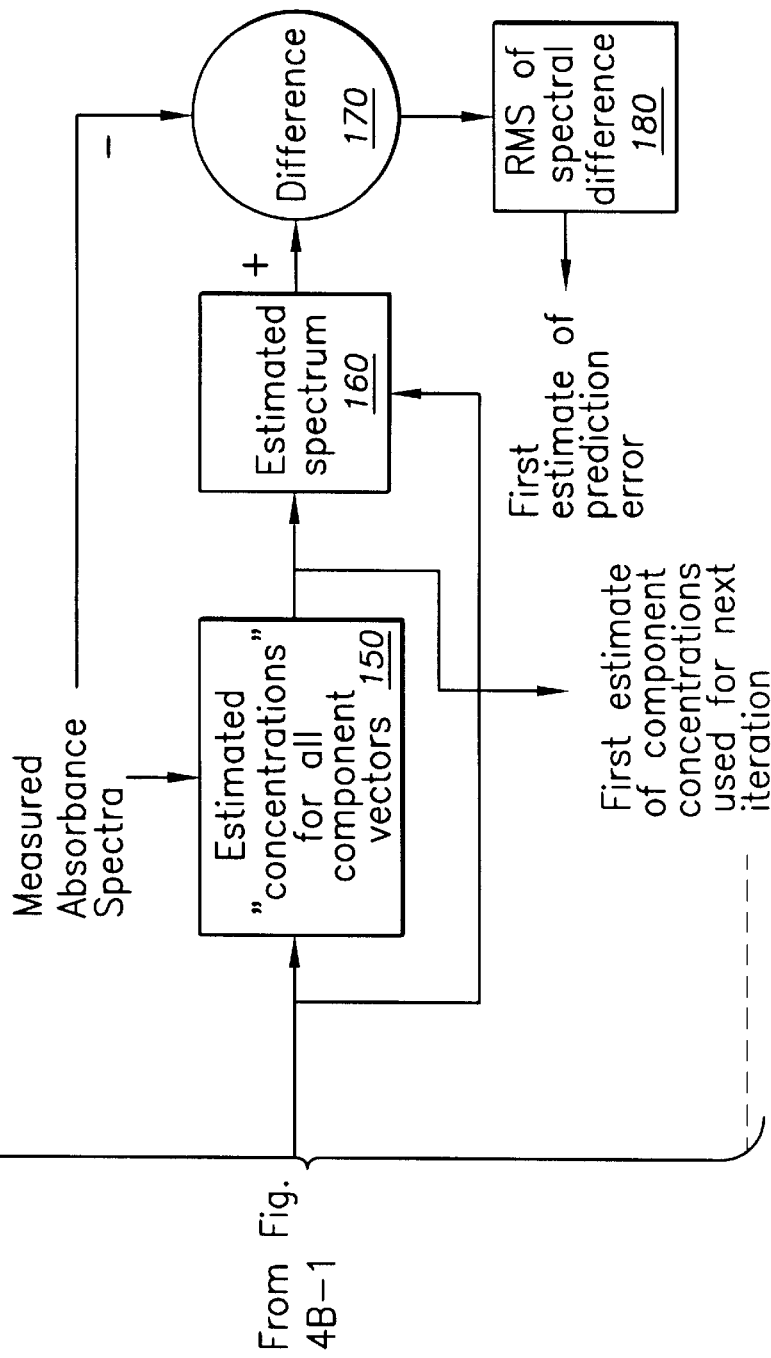

The presently disclosed method 100 for the estimation of component concentrations is outlined in FIG. 4B. The first step 110 determines an estimated pure absorption spectrum from the pure absorption spectra (i.e., the extinction coefficients) of the absorbing pigments and their initial concentration estimates. The residual vector is constrained by the concentration estimate (similar to the way the lysed² vector is constrained) in step 120. At step 130 the estimated spectral correction for path nonuniformity is formed by the creation of the lysed² vector. At step 140 a first trial extinction matrix is determined from the spectral correction for path nonuniformity of step 130, the pseudo-absorption spectra of scatter, the pure absorption spectra and the constrained residual vectors. Analysis (e.g., CLS) of the measured absorption spectrum using the first trial extinction matrix of step 140 determines the estimated concentrations for all component vectors at step 150. Next an estimated spectrum is obtained from the first trial extinction matrix and from the estimated concentrations for all component vectors (step 160). At step 170, the difference between the estimated spectrum and the measured spectrum is taken. At step 180 the root mean square (RMS) of the spectral difference from step 170 is calculated, providing a first estimate of prediction error. This process 100 is then repeated for a fixed number of iterations or until the error is sufficiently reduced. In successive iterations, the initial concentration estimates of the absorbing pigments used to determine the estimated pure absorption spectrum are replaced by their latest estimated concentrations obtained in step 150. The method thus described corrects for; (1) the loss due to scatter that arises from changes in a particle's refractive index due the particle's absorption (anomalous dispersion), (2) the loss due to a power-law type scatter arising from small, non-absorbing particles that have a different refractive index from the media, (3) scatter losses due to limitations of the measurement apparatus (collection limitations), (4) multiple path length effects due to sample obstructions or perturbations (e.g., bubbles and clots), (5) multiple path length effects due to the measurement apparatus (non-collimated probe beam), and (6) multiple path length effects due to all types of scatter (i.e., power-law and anomalous dispersion).

To illustrate the method, consider the measurement of hemoglobin concentration in lysed blood. The vectors used in the analysis are typically the major hemoglobin components of interest (e.g. $O_2Hb$, HHb, COHb, MetHb), the hemoglobin components of minor interest (SulfHb and CNMetHb), and a single vector for scatter as well as possible interferents (e.g., methylene blue). This analysis by prior methods has proven to be inadequate for the accurate measurement of hemoglobin in whole blood.

A power law in wavelength can approximate losses due to non-absorbing particle scatter. Since the spectral shape of this type of scatter as well as its magnitude vary with blood components and chemistry, multiple parameters are required for an adequate characterization.

Additional effects must be included for accurate measurements. As stated above, hemoglobin is concentrated in red blood cells. The short path length required for good signal-to-noise in such systems causes the probe light beam to sample on average only a small number of cells. This small mean sample number implies that significant variations occur in the number of cells sampled by different rays of the probe beam. To adequately model this effect, the total integrated signal can be expressed as an average (summation) over the number of cells sampled where an appropriate distribution function is selected. This distribution function is similar to that needed to model path length distributions discussed in Appendix A. As described above, the effect of these variations on the measured absorption spectrum can be approximated by the square of the pure absorption spectrum. The pure absorption spectrum consists only of the spectra of the absorbing component pigments (i.e., hemoglobin). Note that the square of the measured absorption spectrum (which includes scatter, etc.) does not provide a preferred embodiment of the presently disclosed invention.

Since hemoglobin is a strong absorber, its absorption causes significant variations in the refractive index of the red cells (anomalous dispersion). As discussed in the introduction, this refractive index variation results in additional scatter that is not characterized by a simple power-law and, in fact, depends on the absorption spectrum of hemoglobin itself. Therefore, this form of scatter caused by absorption depends on the hemoglobin composition of the whole blood. In the presently disclosed method, this hemoglobin scatter vector is assumed to add linearly. In other words, the total hemoglobin scatter vector is a linear combination of the hemoglobin scatter vectors of the different hemoglobin components taken separately.

In an additional example, an analysis of hemoglobin in whole blood is shown.

The first step is to determine the vectors that describe hemoglobin scatter.

$$r_{exp} \approx E_{trial} * c_{trial} - a_{measured}$$

Reference values for the samples are then used to determine the individual residual vectors by the following:

$$v_{res} \approx R_{exp} * c'_{ref} * (c_{ref} * c'_{ref})^{-1}$$

In the analysis of complex samples, which includes the estimation of hemoglobin concentrations in whole blood, there may exist unknown components. In certain instances, the instrument or sample effects are difficult to determine by a priori analysis. For example, variations in the refractive index of the sample, also known as anomalous dispersion, cause scatter that varies with the concentration of the sample components. This scatter can be characterized by a method that incorporates known information about the sample by a hybrid method of analysis. Unknown components of the sample or instrument effects can also be treated with this method.

The absorption spectra of a sample (as measured in a non-turbid sample) can be estimated using reference methods to determine the concentrations of the sample components and combining this information with known absorption spectra of the components as shown:

$$a_{ref} \approx E * c_{ref}$$

where:

$a_{ref}$ is the estimated absorption,

E is a matrix of column vectors, each denoting the spectrum of a component or factor at a particular wavelength, and $c_{ref}$ is the estimated concentration from reference methods.

The estimated absorption spectrum is combined with other estimated spectra from known components with unknown concentrations (e.g. scatter and/or the square of the absorption) and the combined spectra used to approximate the measured absorption using known techniques such as Least Squares Estimation (LSE).

$$c_{trial} \approx (E'_{trial} * E_{trial})^{-1} * E'_{trial} * a_{measured}$$

where:

$E_{trial}$ is the combined spectra matrix, and $c_{trial}$ is the vector of estimated concentrations.

The difference or residual between the estimated spectrum and the measured spectrum is the approximation of the unknown component(s). This difference between the estimated spectrum and the measured spectrum is used as a vector or vectors in the analysis of future samples. Techniques such as Partial Least Squares (PLS), Principal Components Regression (PCR) and Classical Least Squares (CLS) can be used to determine vectors from residual spectra. CLS is then used to obtain concentrations of the vectors in a sample. If only a single component is known, then the vector for that single component can be determined via regression techniques of PLS or Principal Component Analysis (PCA) followed by regression testing.

$$r_{exp} \approx E_{trial} * c_{trial} - a_{measured}$$

where:

$r_{exp}$ is the residual spectrum.

The analysis using a single residual vector is shown by:

$$c_{new} \approx (E'_{new} * E_{new})^{-1} * E'_{new} * a_{measured}$$

where:

$E_{new} \equiv [E|v_{res}]$ $v_{res}$ is (are) the vector(s) from the residual term(s), and $c_{new}$ is the vector of estimated concentrations.

The residual vector(s) obtained by this method can be nonlinear if their relative inclusion is dependent on the concentration of the other components. Although all such residual vectors can be included in an analysis, the residual vectors may be related to the concentration of the components and the inclusion of this information reduces the degrees of freedom in the estimate of component concentrations. The reduction in the number of vectors used to fit the measured spectrum significantly reduces the tendency to over-fit the data.

In the case of estimating hemoglobin concentration in whole blood, the effects of anomalous dispersion is directly related to the concentrations of each of the hemoglobin components. A residual vector describing the effect of anomalous dispersion, and other effects, for each of the hemoglobin components is generated in the manner described above. These vectors are shown in FIG. 5A and 5B. FIG. 5A is the vector for oxyhemoglobin. FIG. 5B shows the vectors for all the principal hemoglobin components. A new $E_{trial\_new}$ now includes additional nonlinear vector to describe the contribution from the residual vectors.

$$E_{trial\_new} = [E_{trial} \, V_{residual}]$$

and $$V_{residual} = E_{residual} * c_{hemo\_est},$$

where $E_{residual}$ is the matrix of residual vectors from the principal hemoglobin components.

Theses vectors are now combined to form a single pseudo-absorption vector by multiplying the anomalous dispersion matrix, formed using the individual vectors, by the same vector of estimated relative concentrations hemoglobin used in calculating the lysed$^2$ vector. This new pseudo-absorption vector, like the lysed$^2$ vector, changes with each iteration of the estimated process. The process itself is unchanged.

Figure 6:
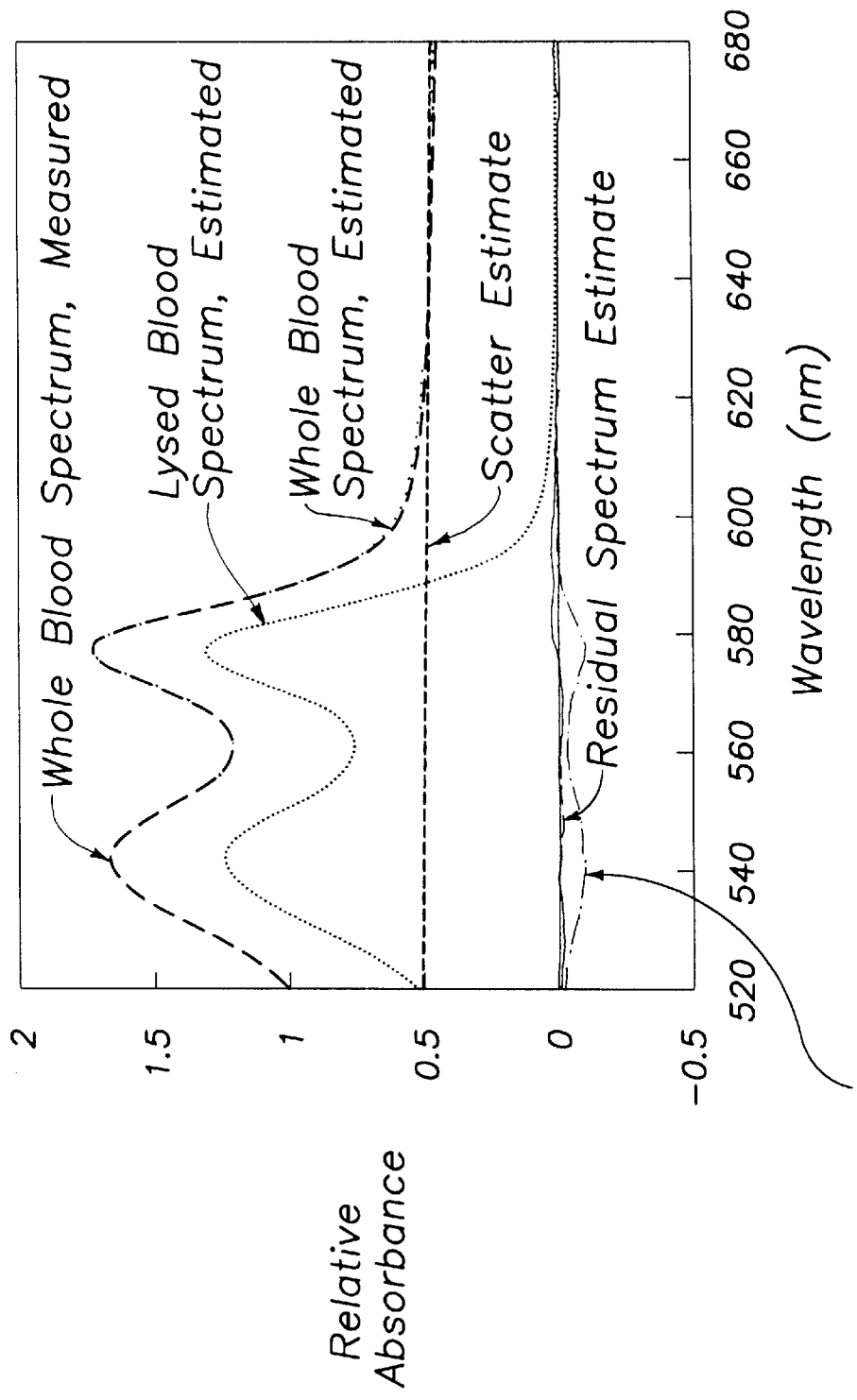
FIG. 6 is a graph of the measured absorption spectrum of whole blood, the estimated absorption spectra of whole blood and each of the estimated components.

The results of an estimation of hemoglobin concentrations in a sample consisting mainly of oxyhemoglobin is shown in FIG. 6. The measured absorption spectrum, the estimated absorption spectrum and the absorption spectra of each of the estimated components is shown in the figure.

The effectiveness of the method for estimating hemoglobin concentrations in whole blood was tested by a protocol consisting of 24 sample types created from male and female donors, using four different hemoglobin compositions at three different total hemoglobin levels for each composition and sex. The results, which can be found in Appendix B, demonstrated that the method can provide accuracy and repeatability nearly equivalent to instruments utilizing lysed blood free from turbidity.

Figure 7:
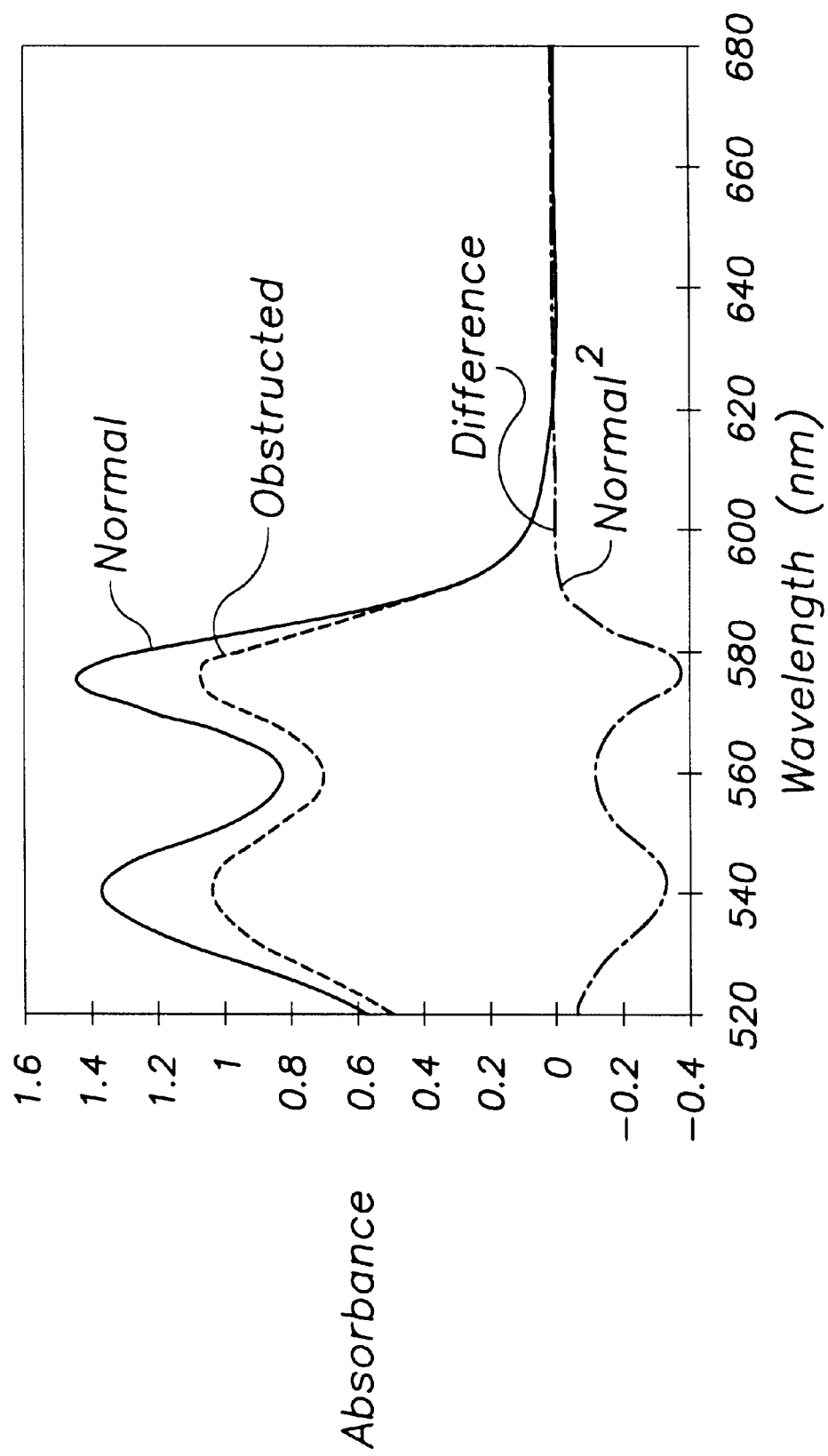
FIG. 7 is a graph of an absorption spectrum of a normal sample and an obstructed sample.

In a specific instance of the analysis of an inhomogeneous sample, the use of a nonlinear component to detect and correct for sample inhomogeneity or instrument effects for lysed blood is shown. In this example, sample chamber obstructions produce an inhomogeneous measurement zone that interferes with normal optical measurements. The nature of many of these obstructions is to create a zone in which blood is excluded. This exclusion results in higher optical transmittance for that area. An example of two sequential samples of the same lysed blood sample is shown in FIG. 7. The sample with the higher absorption gives the normally expected spectrum, as indicated by the waveform labeled "Normal". The sample with the obstruction has an abnormally low absorption, as shown in the waveform labeled "Obstructed". The difference between these spectra is shown as the dotted line labeled "Difference". The difference is modeled by the square of the normal absorption multiplied by a negative constant labeled "Normal$^2$" which almost exactly overlays the "Difference" waveform.

The fractions and tHb levels predicted by a known method are shown below in Table 1. Notice that the tHb level drops and that the fractions change dramatically.

TABLE 1

| | | | Previous Method | | | | | |
|---|---|---|---|---|---|---|---|---|
| tHb | HHb | O2Hb | COHb | MetHb | Scatter1 | Scatter2 | Lysed$^2$ | FIT |
| 14.79 | −1.94 | 102 | 0.63 | −0.4 | −0.7 | | | 1.63E-04 |
| 12.37 | 8.17 | 82.39 | 3.24 | 6.2 | −1.06 | | | 2.23E-03 |

The fractions and tHb levels predicted for the same two samples using the presently disclosed method are shown below in Table 2. In this instance the tHb change is less than 0.3 g/dL and the worst case fraction change is only approximately 2%. It should also be noted that the Lysed$^2$ estimate is a relatively large negative value for the obstructed sample as compared with the normal sample. The large negative value is typical for most obstructions, though some obstructions can cause positive values.

TABLE 2

Presently Disclosed Method

| tHb | HHb | O2Hb | COHb | MetHb | Scatter1 | Scatter2 | Lysed[2] | FIT |
|---|---|---|---|---|---|---|---|---|
| 14.49 | −0.73 | 99.91 | 0.69 | 0.13 | −1.15 | 0.36 | 0.00592 | 7.68E-05 |
| 14.22 | −2.22 | 99.16 | 2.75 | 0.31 | 0.76 | −0.58 | −0.0428 | 1.95E-04 |

The present method operates by first estimating the fractions (100% O2Hb is assumed) then using the square of this spectrum as an additional component in the least squares analysis. The square of the new estimated spectrum (based on the resulting fractions obtained in the least squares estimation) is then incorporated and the process is then repeated until the fraction values converge. Typically only 2 or 3 iterations are required if the first estimate is good.

The convergence process is illustrated below in Table 3 using the obstructed sample as an example.

TABLE 3

Convergence of the Presently Disclosed Method with an Obstructed Sample

| tHb | HHb | O2Hb | COHb | MetHb | Scatter1 | Scatter2 | Lysed[2] | FIT |
|---|---|---|---|---|---|---|---|---|
| 14.25 | −1.69 | 99.15 | 2.25 | 0.3 | 0.81 | −0.69 | −0.0430 | 2.14E-04 |
| 14.22 | −2.2 | 99.15 | 2.73 | 0.31 | 0.76 | −0.58 | −0.0428 | 1.95E-04 |
| 14.22 | −2.22 | 99.16 | 2.75 | 0.31 | 0.76 | −0.58 | −0.0428 | 1.95E-04 |

Figure 8:
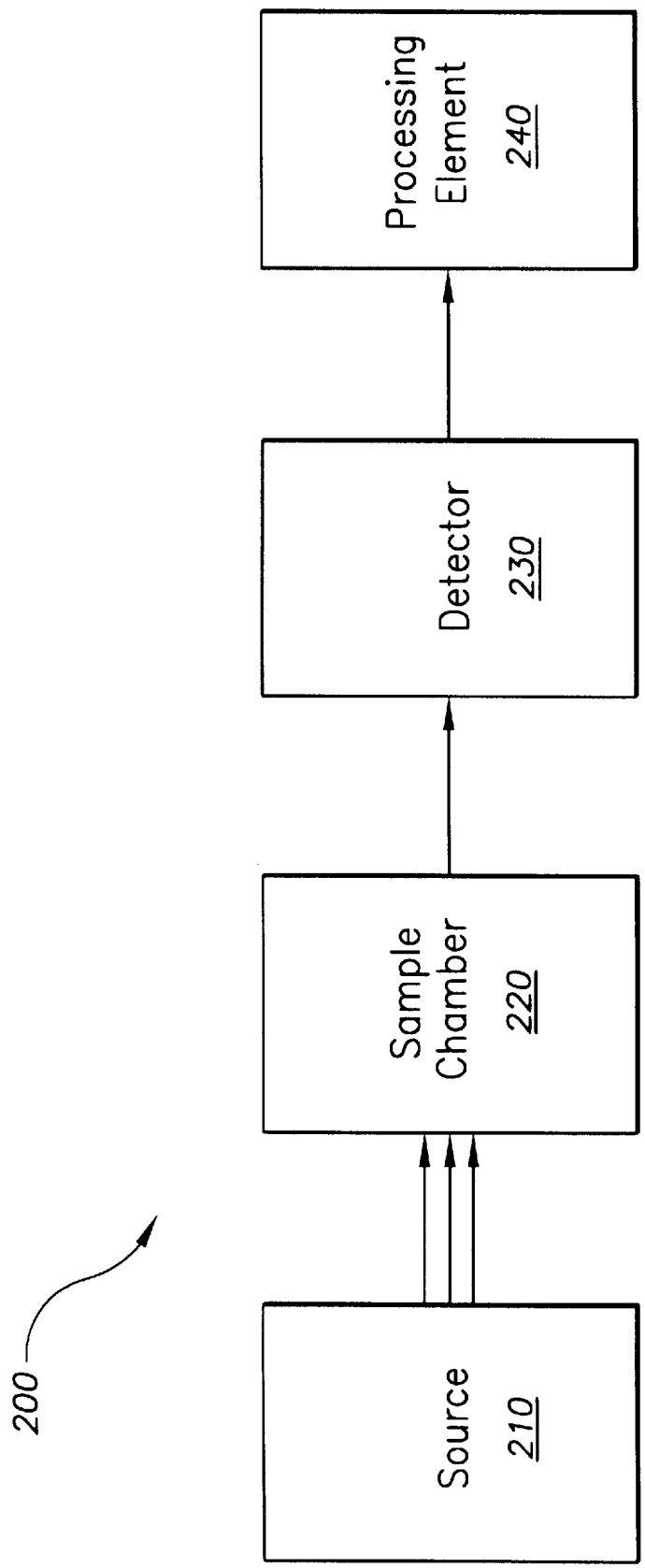
FIG. 8 is a block diagram of a spectrometer used in the present invention.

Referring now to FIG. 8, a measurement apparatus for performing spectroscopic analysis for determining estimated concentrations of one or more components of a multi-component sample is shown. The measurement apparatus 200 comprises an excitation source 210 that provides an excitation signal to a sample chamber 120. Sample chamber 120 includes a multi-component sample therein. A detector 130 receives the excitation signal that may be modified by the sample within the sample chamber 220. Processing element 240 is coupled to or may be integrated with, detector 230 and determines the concentrations of components of the multi-component sample. This determination includes the method described above in that the nonlinear effects are taken into account as part of the determination and thus provide a more accurate estimation of the component concentration of the multi-component sample.

As shown above the presently disclosed method and apparatus provides for more accurate analysis of samples having turbidity and/or high absorption by taking into account the effect of nonlinear parameters on the measurement. The nonlinear term is incorporated into the multivariate analysis resulting in increased accuracy of the analysis.

Having described preferred embodiments of the invention it will now become apparent to those of ordinary skill in the art that various modifications could be made to the presently disclosed invention. It is therefore submitted that the invention should not be limited to the described embodiments, but only by the spirit and scope of the appended claims.

APPENDIX A

Total transmittance through a sample is calculated as the sum total of the transmittance of all light rays of the probe light beam detected by the detector. When the sample is inhomogeneously absorbing and/or when the path of light through the sample is not single-valued, different light rays through the sample will experience different absorbing path lengths (i.e., multiple path lengths). In this case, the total transmitted signal can be modeled as an average (integral) over the transmitted light rays of the probe beam with an appropriately chosen distribution function. This distribution function must accurately reflect the distribution of path lengths experienced by the light rays. Situations in which multiple path lengths can arise include transmission measurements in turbid, lysed blood or whole blood, reflection measurements, the use of imperfectly collimated light in transmission measurements, and the presence of bubbles and/or obstructions in the sample. Absorption, as described earlier, is the negative log of transmittance. For simplicity and without loss of generality, consider only two monochromatic light rays of equal intensity that traverse a non-turbid sample via different path lengths. As an example, assume one light ray encounters a small air bubble in the absorbing sample while the other travels through only sample. Both light rays travel the same geometric distance through the sample cell. The absorption of the two rays may be written as $\alpha$ and $\alpha+2\delta$ respectively, where $\alpha$ is the absorption of the light ray that encounters a bubble and $2\delta$ is the absorption difference (=gain in absorption because the bubble excluded absorbing sample) between the two rays. The total transmitted power is the average of the transmitted power of all rays weighted by their individual strengths. In this simple example with two rays of identical strength, the total absorption measured is then given by $$Abs = -\ln[(e^{-\alpha} + e^{-\alpha-2\delta})/2]$$

This expression can be simplified by removing the common factor $e^{-\alpha}$.

$$Abs = \alpha - \ln\ e^{-\alpha} - \ln[(1+e^{-2\delta})/2]$$

or $$Abs = \alpha - \ln[(1+e^{-2\delta})/2]$$

The exponential and natural log can be expanded into a Taylor series as follows:

$$e^x = 1 + x - + x^2/2 + x^3/3! - \ldots$$

$$\ln(1+x) = x - x^2/2 + x^3/3 - \ldots$$

Using these expansions in the expression for absorption gives:

$$Abs = \alpha - \delta + \delta^2 - 2\delta^3/3 + \ldots$$

For reasonably small values of $\delta$ the above expression can be simplified to:

$$Abs = \alpha - \delta + \delta^2$$

Note that the first two terms are essentially the arithmetic average of the absorption for the two rays. Also note that the difference between the absorption of the two rays, $\delta$, is proportional to $\alpha$, the absorption coefficient of the sample. The above expression then becomes:

$$Abs = \alpha_{ave} - k^* \alpha^2$$

where k is a proportionality constant.

It should be noted that this expression is in the form of the approximation used to model the nonlinear effects on the measured absorption $\alpha$. We refer to $\alpha^2$ as the lysed-squared (or lysed$^2$) term (vector). While the constant k can be calculated in this simple example, it is left as a weighting factor in the least squares analysis of actual samples. In this way, k is determined to give the best fit of the predicted absorption spectrum to the actual spectrum. The magnitude of k measures the extent to which any of the above phenomena that can lead to multiple path length effects occurs in the measurement. Because the lysed-squared term depends on the sample's pure absorption spectrum, it requires knowledge of the concentrations of the components in the sample. (Note that "pure" absorption spectrum is the spectrum that would occur if the sample had no turbidity or other scatter effects.) Therefore, the present method must use an iterative process in which the lysed-squared term is treated as an additional linear term that is fixed for the iterative step. After each iteration, it is updated to reflect the latest estimate of component concentrations and then used in the least squares analysis of the next iteration. This process converges quickly to the best estimate and is described further in the test of this patent. It should also be noted that higher order terms in the above expansion can be included in the analysis described herein as needed.

Figure 3A:
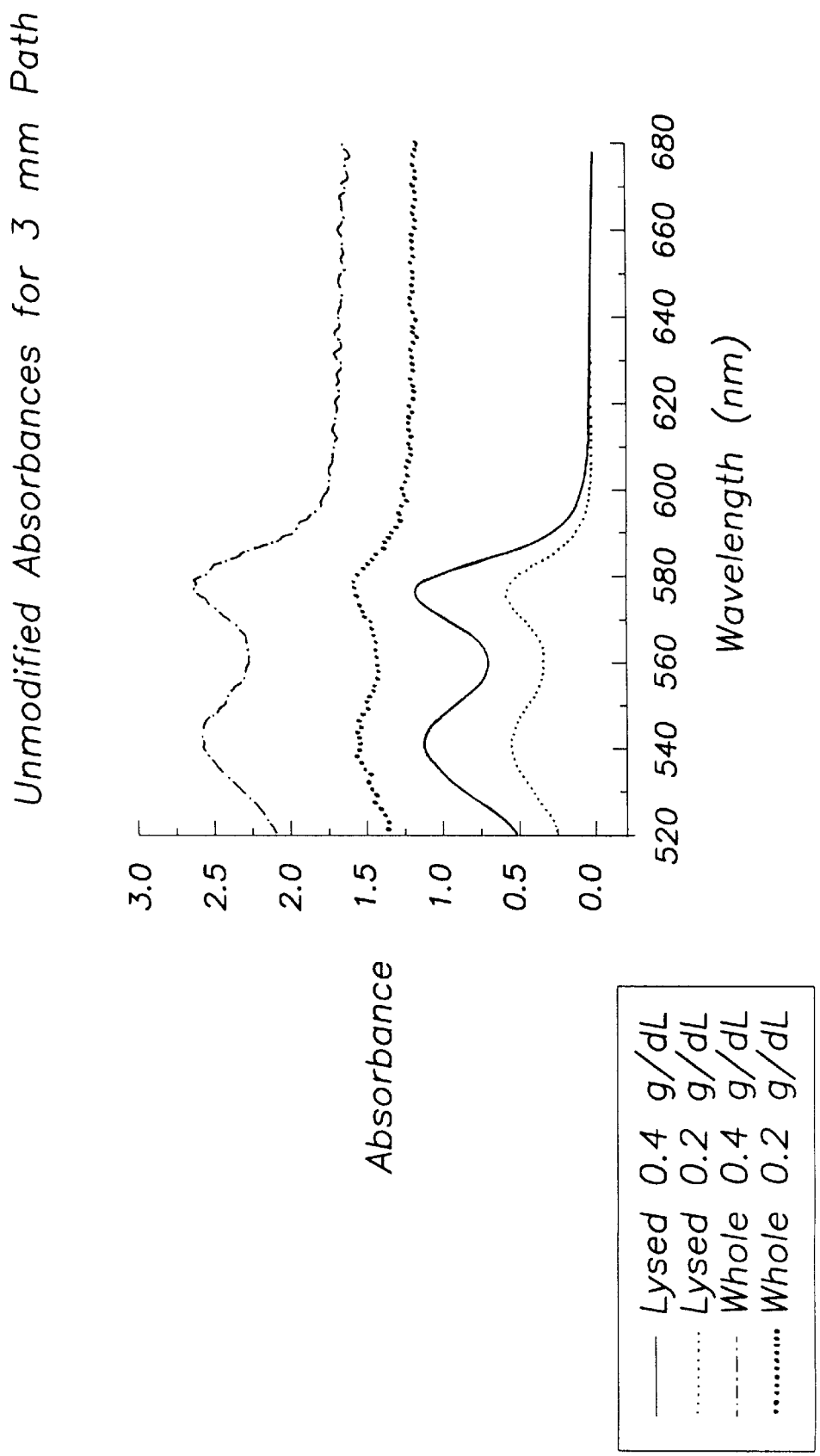
FIG. 3A is a plot of absorption spectra for whole and lysed blood a two different hemoglobin concentrations.
Figure 3B:
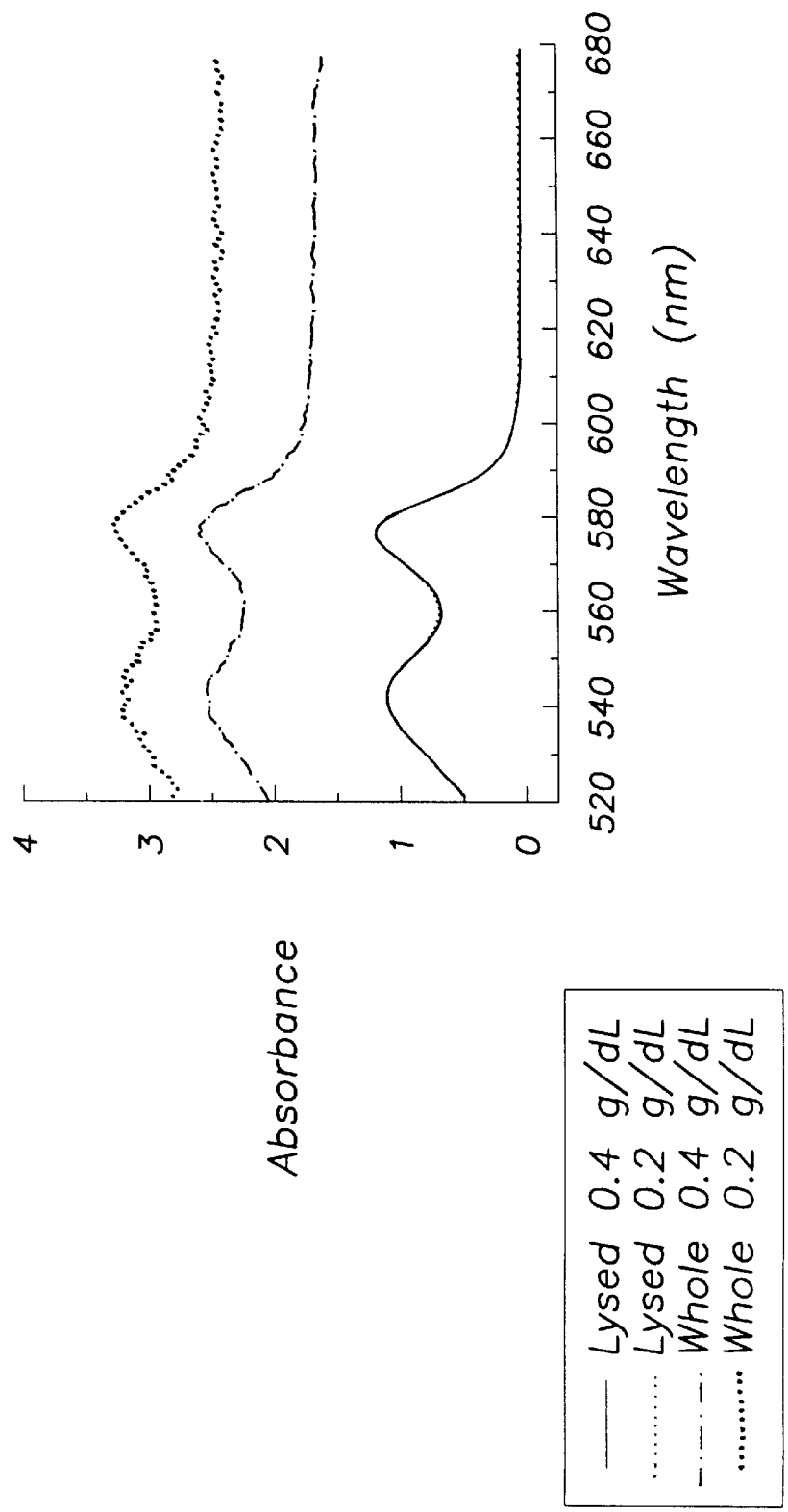
FIG. 3B is a plot of scaled absorption spectra.
Figure 3C:
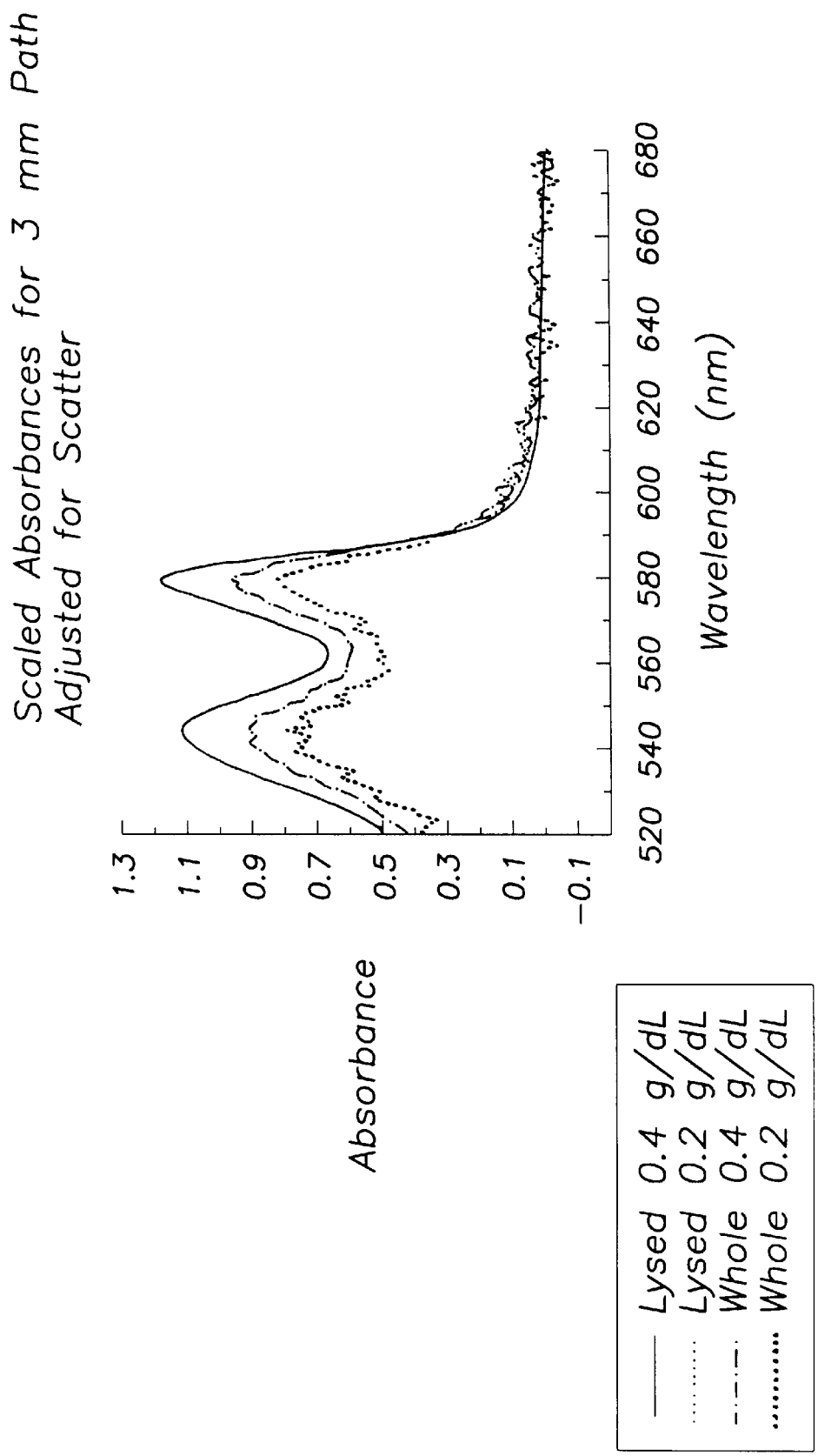
FIG. 3C is a plot of scaled absorption spectra adjusted for scatter.
Figure 3D:
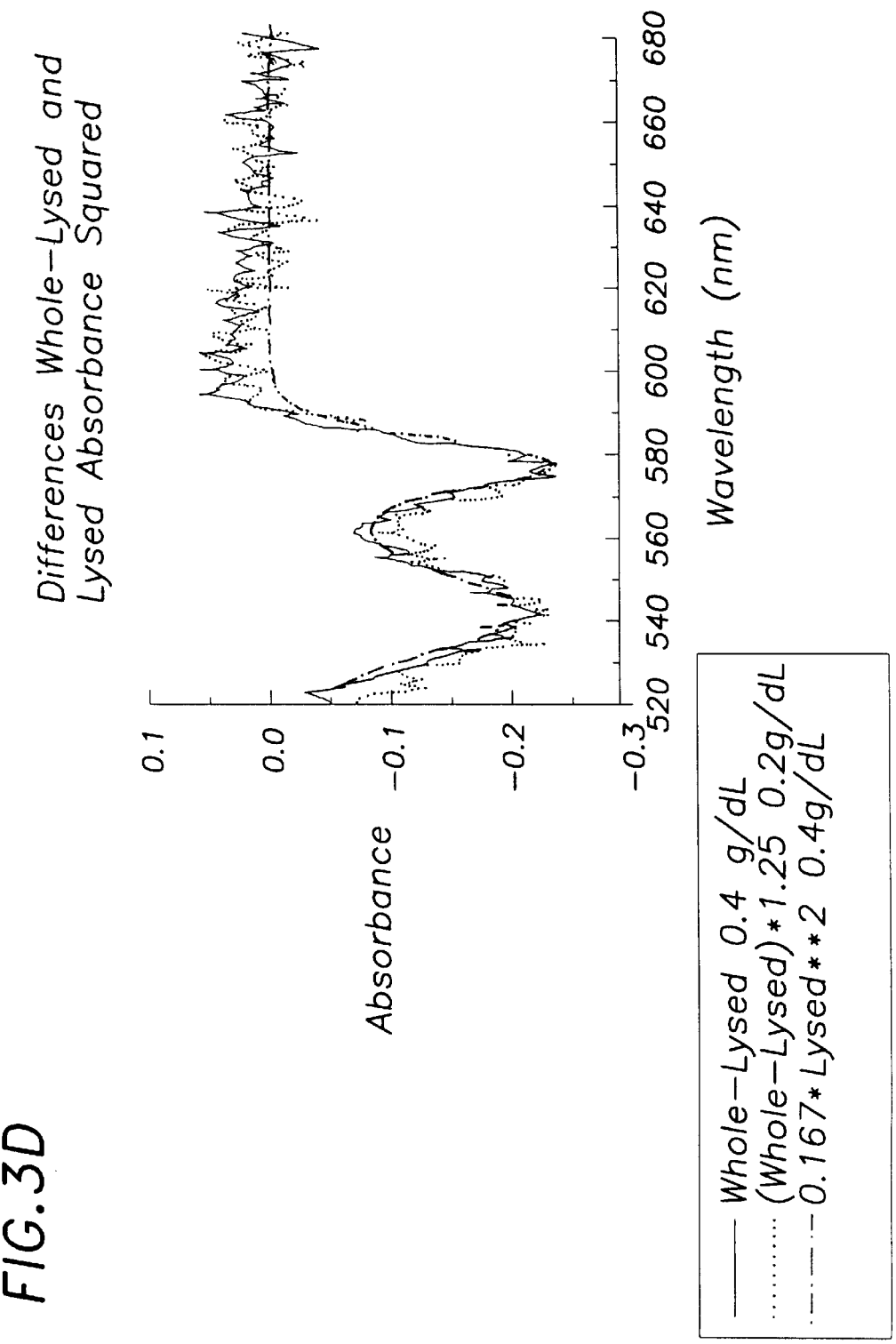
FIG. 3D is a plot of absorption spectra of the whole minus lysed blood sample and the lysed-squared vector.

In an experiment performed with a Cary IV Spectrophotometer (Varian Associates, Palo Alto Calif.), the absorption spectra of diluted whole and lysed blood were measured in stirred cuvettes. Two different concentrations of hemoglobin were measured, 0.2 and 0.4 g/dL. These concentrations are low compared with normal whole blood, but were selected to allow the use of a 3 mm path length cuvette and to avoid excess absorption at the peak absorbing wavelengths. FIG. 3A shows the spectra of the four samples as measured on the Cary IV. In FIG. 3B, these spectra have been scaled for the differences in hemoglobin concentration but have not been corrected for scatter. In FIG. 3C, a scatter correction using a simple power law of wavelength was applied. The lysed blood spectra at each hemoglobin concentration were subtracted from the whole blood spectra. The difference for the 0.2 g/dL samples was scaled by a factor of 1.25 to provide a visual match to the 0.4 g/dL sample difference. These differences are shown in a graph (see FIG. 3D) along with a plot of the square of the lysed blood spectrum (scaled to demonstrate the close match of this correction with the above differences). The remaining error is substantially corrected for with another correction term described in this patent.

APPENDIX B

Errors After Linear Correlation Correction

|   | tHb | HHb | O2Hb | COHb | MetHb |
|---|---|---|---|---|---|
| m | 0.052121 | 0.066035 | −0.22398 | −0.00264 | 0.166204 |
| b | −0.222 | −0.1007 | 3.519 | −0.57259 | −3.06 |

Reference w/ adj

|    | tHb Err | HHb Err | O2Hb Err | COHb Err | MetHb Err |
|----|---------|---------|----------|----------|-----------|
| 1  | 0.3  | 0.0  | −0.3 | 1.0  | −0.8 |
| 2  | 0.3  | 0.1  | 0.0  | 0.2  | −0.3 |
| 3  | 0.3  | −0.4 | 0.2  | 1.0  | −0.8 |
| 4  | 0.2  | 0.0  | 0.0  | 0.8  | −0.9 |
| 5  | 0.2  | −0.1 | 0.0  | 0.4  | −0.3 |
| 6  | 0.0  | −0.6 | −9.1 | −0.7 | 10.5 ?????? |
| 7  | 0.2  | −0.2 | −0.5 | 0.3  | 0.3 |
| 8  | −0.3 | 0.6  | −0.7 | −0.5 | 0.7 |
| 9  | 0.3  | −0.1 | −0.8 | 0.4  | 0.4 |
| 10 | 0.1  | 0.2  | −0.6 | −0.2 | 0.6 |
| 11 | −0.6 | 1.8  | −1.9 | −1.6 | 1.9 |
| 12 | −0.6 | −5.4 | 2.5  | −10.8 | 29 ?????? |
| 13 | −0.1 | −0.6 | 0.0  | 0.5  | 0.2 |
| 14 | −0.2 | −0.1 | 0.4  | −0.7 | 0.4 |
| 15 | 0.1  | −0.6 | 0.4  | 0.1  | 0.2 |
| 16 | 0.0  | −0.3 | 0.3  | 0.3  | −0.2 |
| 17 | −0.1 | 0.1  | 0.5  | −0.7 | 0.0 |
| 18 | 0.0  | −0.3 | 1.3  | −0.8 | −0.3 |
| 19 | 0.0  | −0.3 | 1.0  | −0.5 | −0.3 |
| 20 | −0.1 | 0.1  | 0.0  | −0.2 | −0.1 |
| 21 | −0.1 | −0.4 | 0.3  | 0.8  | −0.8 |
| 22 | −0.2 | 0.0  | 0.8  | −0.6 | −0.2 |
| 23 | −0.2 | 0.2  | 0.1  | −0.5 | 0.2 |
| 24 | −0.1 | 0.2  | −0.6 | 0.5  | −0.1 |

| | | | | | | P21 Analysis Results | | | | | | |
|---|---|---|---|---|---|---|---|---|---|---|---|---|
| Means | tHb | HHb | O2Hb | COHb | MetHb | SulfHb | Scat .2 | Scat 2.5 | O2Hb^2 | sqt | Flt | |
| | | | Double Pass using 800 Series Ext. Coef. w/ Scatter .2 & 2.5 plus ext_coef^2 and sq8t compensation | | | | | | | | | |
| 1 | 6.6 | 0.4 | 99.1 | 0.9 | −0.7 | 0.3 | 38.1 | 3.4 | −0.07 | 78.73 | 9.0E−05 | |
| 2 | 15.3 | 1.0 | 98.1 | 0.4 | 0.3 | 0.2 | 53.1 | 2.3 | −0.11 | 97.42 | 9.7E−05 | |
| 3 | 21.4 | 0.9 | 96.5 | 1.9 | 0.6 | 0.1 | 55.6 | 3.8 | −0.11 | 115.46 | 2.7E−04 | |
| 4 | 6.5 | 0.3 | 99.4 | 0.7 | −0.7 | 0.3 | 39.5 | 3.1 | −0.07 | 76.87 | 9.0E−05 | |
| 5 | 15.2 | 0.8 | 98.3 | 0.6 | 0.2 | 0.2 | 55.6 | 2.3 | −0.11 | 99.63 | 1.3E−04 | |
| 6 | 21.1 | 0.7 | 87.3 | 0.2 | 11.8 | 0.0 | 56.4 | 3.9 | −0.12 | 106.06 | 2.4E−04 | Mislabel |
| 7 | 6.4 | 0.1 | 77.8 | 22.0 | −0.2 | 0.3 | 42.1 | 2.6 | −0.07 | 75.2 | 1.2E−04 | |
| 8 | 14.8 | 1.5 | 77.8 | 19.5 | 1.1 | 0.1 | 52.9 | 5.7 | −0.15 | 62.5 | 2.2E−04 | |
| 9 | 21.4 | 1.2 | 76.3 | 20.8 | 1.5 | 0.2 | 56.3 | 3.4 | −0.23 | 78.2 | 3.7E−04 | |
| 10 | 6.3 | 0.5 | 77.7 | 21.5 | 0.1 | 0.1 | 40.2 | 4.3 | −0.07 | 68.8 | 1.4E−04 | |
| 11 | 14.5 | 2.7 | 76.7 | 18.5 | 2.3 | −0.2 | 48.8 | 9.2 | −0.18 | 33.6 | 3.4E−04 | |
| 12 | 20.5 | 6.7 | 79.9 | 9.6 | 3.9 | 0.0 | 43.0 | 19.7 | −0.62 | −113.5 | 5.3E−04 | ?????? |
| 13 | 6.1 | −0.3 | 88.7 | 0.8 | 10.7 | 0.1 | 41.2 | 2.9 | −0.08 | 79.7 | 1.0E−04 | |
| 14 | 14.6 | 0.8 | 89.2 | −0.8 | 10.7 | 0.1 | 43.2 | 4.3 | −0.09 | 87.7 | 1.7E−04 | |
| 15 | 21.1 | 0.7 | 87.3 | 0.2 | 11.8 | 0.0 | 56.4 | 3.9 | −0.12 | 106.1 | 2.4E−04 | |
| 16 | 6.2 | 0.0 | 89.1 | 0.6 | 10.3 | 0.1 | 45.5 | 2.5 | −0.08 | 80.1 | 1.7E−04 | |
| 17 | 14.8 | 1.0 | 89.2 | −0.7 | 10.3 | 0.1 | 42.6 | 4.4 | −0.08 | 87.9 | 1.5E−04 | |
| 18 | 20.9 | 1.0 | 88.3 | −0.7 | 11.4 | 0.2 | 57.1 | 4.0 | −0.12 | 91.5 | 3.6E−04 | |
| 19 | 6.4 | 0.1 | 89.5 | 6.2 | 4.0 | 0.3 | 38.9 | 2.6 | −0.07 | 78.1 | 1.0E−04 | |
| 20 | 14.7 | 1.0 | 88.2 | 5.5 | 5.0 | 0.2 | 44.9 | 3.0 | −0.09 | 91.3 | 1.6E−04 | |
| 21 | 21.0 | 0.9 | 86.7 | 6.8 | 5.4 | 0.2 | 61.0 | 3.1 | −0.11 | 103.1 | 4.1E−04 | |
| 22 | 6.2 | 0.3 | 89.3 | 6.1 | 4.1 | 0.2 | 41.2 | 3.8 | −0.08 | 72.6 | 1.4E−04 | |
| 23 | 14.6 | 1.0 | 88.2 | 5.2 | 5.4 | 0.2 | 45.0 | 3.8 | −0.11 | 81.9 | 1.7E−04 | |
| 24 | 21.0 | 1.5 | 85.9 | 6.4 | 6.2 | 0.0 | 61.3 | 4.5 | −0.18 | 81.4 | 3.6E−04 | |
| | | | | | | WRSDs | | | | | | |
| 1.5 | 0.0 | 0.1 | 0.1 | 0.2 | 0.0 | 0.0 | 0.5 | 0.3 | 0.0 | 1.2 | 3.4E−06 | |
| 2.5 | 0.1 | 0.1 | 0.1 | 0.1 | 0.1 | 0.0 | 0.2 | 0.1 | 0.0 | 1.4 | 1.4E−05 | |
| 3.5 | 0.2 | 1.0 | 0.9 | 1.8 | 0.2 | 0.1 | 1.4 | 1.5 | 0.0 | 19.8 | 1.4E−04 | |
| 4.5 | 0.1 | 0.1 | 0.3 | 0.1 | 0.3 | 0.0 | 2.3 | 0.1 | 0.0 | 1.2 | 6.5E−07 | |
| 5.5 | 0.2 | 0.2 | 0.2 | 0.4 | 0.1 | 0.0 | 1.5 | 0.1 | 0.0 | 4.3 | 4.4E−05 | |
| 6.5 | 0.0 | 0.2 | 0.6 | 0.6 | 0.2 | 0.1 | 1.2 | 0.9 | 0.0 | 10.3 | 1.0E−04 | Mislabel |
| 7.5 | 0.0 | 0.3 | 0.2 | 0.5 | 0.1 | 0.0 | 0.9 | 0.5 | 0.00 | 3.0 | 5.5E−06 | |
| 8.5 | 0.1 | 0.5 | 0.6 | 1.2 | 0.4 | 0.1 | 1.3 | 1.0 | 0.03 | 11.8 | 4.8E−05 | |
| 9.5 | 0.0 | 0.5 | 0.2 | 0.8 | 0.6 | 0.1 | 1.2 | 1.1 | 0.00 | 14.8 | 1.3E−05 | |
| 10.5 | 0.1 | 0.2 | 0.1 | 0.3 | 0.1 | 0.0 | 0.5 | 0.4 | 0.00 | 2.4 | 2.9E−05 | |
| 11.5 | 0.0 | 0.1 | 0.2 | 0.2 | 0.1 | 0.0 | 0.6 | 0.8 | 0.01 | 5.6 | 2.2E−05 | |
| 12.5 | 0.2 | 0.1 | 0.4 | 0.2 | 0.1 | 0.1 | 0.6 | 0.9 | 0.01 | 2.0 | 2.9E−05 | ?????? |
| 13.5 | 0.1 | 0.2 | 0.4 | 0.4 | 0.1 | 0.0 | 0.3 | 0.0 | 0.00 | 1.9 | 5.6E−06 | |
| 14.5 | 0.1 | 0.2 | 0.1 | 0.3 | 0.1 | 0.0 | 1.1 | 0.2 | 0.01 | 2.4 | 3.8E−05 | |
| 15.5 | 0.0 | 0.2 | 0.6 | 0.6 | 0.2 | 0.1 | 1.2 | 0.9 | 0.01 | 10.3 | 1.0E−04 | |
| 16.5 | 0.1 | 0.2 | 0.3 | 0.3 | 0.2 | 0.0 | 5.3 | 0.5 | 0.00 | 2.1 | 4.7E−05 | |
| 17.5 | 0.1 | 0.0 | 0.3 | 0.1 | 0.3 | 0.0 | 0.0 | 0.8 | 0.01 | 2.5 | 3.7E−06 | |
| 18.5 | 0.4 | 0.8 | 0.7 | 1.4 | 0.2 | 0.1 | 1.6 | 1.3 | 0.02 | 18.9 | 1.3E−04 | |
| 19.5 | 0.1 | 0.3 | 0.1 | 0.3 | 0.1 | 0.0 | 1.4 | 0.1 | 0.00 | 1.3 | 4.9E−06 | |
| 20.5 | 0.0 | 0.8 | 0.2 | 1.1 | 0.0 | 0.0 | 0.5 | 0.6 | 0.01 | 9.5 | 2.5E−05 | |
| 21.5 | 0.1 | 0.3 | 0.5 | 0.7 | 0.2 | 0.1 | 1.0 | 0.8 | 0.02 | 11.2 | 1.7E−04 | |
| 22.5 | 0.3 | 0.1 | 0.2 | 0.0 | 0.1 | 0.1 | 0.8 | 1.2 | 0.01 | 5.0 | 2.4E−05 | |
| 23.5 | 0.3 | 0.4 | 0.4 | 0.7 | 0.5 | 0.1 | 1.5 | 0.4 | 0.03 | 7.5 | 4.7E−05 | |
| 24.5 | 0.1 | 0.7 | 1.0 | 1.0 | 1.1 | 0.1 | 0.5 | 1.5 | 0.12 | 36.3 | 1.5E−04 | |

Note  Outlier and was not included: Sample 20,2 Sample 12,1

What is claimed is:

1. A method for determining estimations of the concentration of one or more components of a multi-component sample using spectroscopic analysis comprising the steps of:
   estimating a matrix of vectors which represent the significant pure and homogenous spectra of pigments in the sample and of vectors which represent scatter;
   estimating concentrations of one or more components of said multi-component sample;
   using the estimated component concentrations to better refine the vectors representing the nonlinear contributions; and
   repeating the process until a satisfactory estimate of component concentrations is obtained.

2. The method of claim 1 wherein said non-linear contributions are selected from the group consisting of change in refractive index due to high sample absorption, power-law scatter related to particles having a different refractive index from a media, scatter due to sample absorption, scatter losses as measured in a non-absorbing sample, variable path length effects due to said sample, and variable path length effects due to a measurement device.

3. The method of claim 1 wherein said nonlinear contributions comprise the square of the pure absorption.

4. The method of claim 2 wherein said nonlinear contributions comprise higher order terms of the absorption in the expansion of the transmission of said multi-component sample.

5. The method of claim 2 wherein said variable path length effects due to said sample comprises variable path length effects due to the presence of a bubble within said sample.

6. The method of claim 2 wherein said variable path length effects due to said sample comprises variable path length effects due to the presence of an obstruction within said sample.

7. The method of claim 1 wherein said multi-component sample comprises lysed blood.

8. The method of claim 7 wherein said nonlinear contributions comprise variable path length effects due to said sample including a clot.

9. The method of claim 7 wherein said nonlinear contributions comprise the square of the lysed blood absorption.

10. A method of determining a residual vector for determining estimations of concentrations of one or more individual components of a multi-component sample comprising the steps of:

determining a first matrix from an estimated pure absorption spectrum, an estimated spectral correction for path non-uniformity, and a scattered pseudo-absorption spectrum;

determining estimated concentrations for all component vectors by combining said first matrix with a measured first absorption spectrum;

establishing an estimated spectrum from said estimated concentrations for all component vectors and said first matrix; and determining a residual vector from said estimated spectrum and said measured first absorption spectrum.

11. The method of claim 10 wherein said step of determining a residual vector includes taking the difference between said measured first absorption spectrum and said estimated spectrum.

* * * * *